United States Patent [19]

Gebauer

[11] Patent Number: 4,496,748

[45] Date of Patent: Jan. 29, 1985

[54] SUBSTITUTED MACROBICYCLIC ETHERS, THE MANUFACTURE AND USE THEREOF

[75] Inventor: Helmut Gebauer, Munich, Fed. Rep. of Germany

[73] Assignee: Consortium Für Elektrochemische Industrie GMBH, Munich, Fed. Rep. of Germany

[21] Appl. No.: 404,984

[22] Filed: Aug. 4, 1982

[30] Foreign Application Priority Data

Sep. 24, 1981 [DE] Fed. Rep. of Germany ....... 3137939

[51] Int. Cl.$^3$ ............................................ C07D 311/94
[52] U.S. Cl. .................................. 549/396; 549/462; 252/522 R
[58] Field of Search ............................... 549/396, 462

[56] References Cited

U.S. PATENT DOCUMENTS

| | | | |
|---|---|---|---|
| 4,222,904 | 9/1980 | Meins et al. | 549/462 |
| 4,268,445 | 5/1981 | Kropp et al. | 549/396 |
| 4,360,468 | 11/1982 | Upadek et al. | 549/462 |

Primary Examiner—Nicky Chan
Attorney, Agent, or Firm—Collard, Roe & Galgano

[57] ABSTRACT

The invention relates to 13-oxabicyclo[10.3.0]pentadecanes alkylated in the 14-position and, optionally, in the 15-position and to 13-oxabicyclo[10.4.0]hexadecanes alkylated in the 14-position and, optionally, in the 16-position. The compounds according to the invention may be used as odorizers.

2 Claims, No Drawings

SUBSTITUTED MACROBICYCLIC ETHERS, THE MANUFACTURE AND USE THEREOF

The present invention relates to substituted macrobicyclic ethers, the manufacture and use thereof.

De-OS No. 28 10 107 describes 13-oxabicyclo[10.3.0-]pentadecane, a compound which is numbered amongst the macrobicyclic ethers. The compound mentioned can be obtained in a 4-stage process starting from cyclododecanone and bromoacetic ester. It is used as an odorizer having a warm amber fragrance.

The problem of the invention was to find new odorizers.

In a selection of alkyl-substituted and/or alkenyl-substituted 13-oxabicyclopentadecanes and 13-oxabicyclohexadecanes, a group of odorizers has now been found that has a wide range of different scents.

The invention provides compounds of the general formula

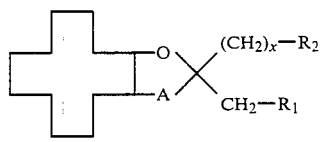

wherein $R_1$ and $R_2$ represent hydrogen or optionally branched alkyl groups having from 1 to 6 carbon atoms or optionally branched alkenyl groups having from 3 to 6 carbon atoms, A represents a bivalent hydrocarbon radical of the general formula

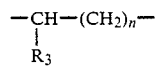

wherein $R_3$ represents hydrogen or methyl, and n and x have, in each case, the same numerical value of 0 or 1.

Compounds according to the invention having from 15 to 21 carbon atoms per molecule are preferred. Compounds having from 15 to 17 carbon atoms per molecule are especially preferred.

Accordingly, $R_1$ and $R_2$ preferably represent hydrogen or methyl.

The invention includes both 13-oxabicyclo[10.3.0-]pentadecanes of the formula

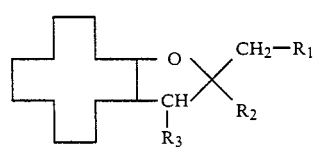

and 13-oxabicyclo[10.4.0]hexadecanes of the formula

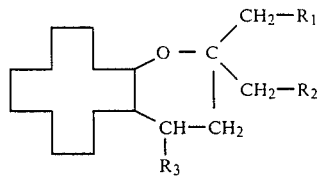

Examples of compounds according to the invention are:
14-methyl-13-oxabicyclo[10.3.0]pentadecane
14,14-dimethyl-13-oxabicyclo[10.3.0]pentadecane
14-ethyl-13-oxabicyclo[10.3.0]pentadecane
14-propyl-13-oxabicyclo[10.3.0]pentadecane
14-isopropyl-14-methyl-13-oxabicyclo[10.3.0]pentadecane
14-butyl-13-oxabicyclo[10.3.0]pentadecane
14-pentyl-13-oxabicyclo[10.3.0]pentadecane
14-isopentyl-13-oxabicyclo[10.3.0]pentadecane
14-hexyl-13-oxabicyclo[10.3.0]pentadecane
14-isohexyl-13-oxabicyclo[10.3.0]pentadecane
14,15-dimethyl-13-oxabicyclo[10.3.0]pentadecane
14-ethyl-15-methyl-13-oxabicyclo[10.3.0]pentadecane
14-propyl-15-methyl-13-oxabicyclo[10.3.0]pentadecane
14-isobutyl-15-methyl-13-oxabicyclo[10.3.0]pentadecane
14-(but-3-en-1-yl)-13-oxabicyclo[10.3.0]pentadecane
14-(but-3-en-1-yl)-15-methyl-13-oxabicyclo[10.3.0]pentadecane
14-pentenyl-13-oxabicyclo[10.3.0]pentadecane
14-(2-methyl-pent-4-en-1-yl)-14-methyl-13-oxabicyclo[10.3.0]pentadecane
14-(2-methyl-pent-4-en-1-yl)-14,15-dimethyl-13-oxabicyclo[10.3.0]-pentadecane
14,14-diethyl-13-oxabicyclo[10.3.0]pentadecane
14,14,15-trimethyl-13-oxabicyclo[10.3.0]pentadecane
14,14-diethyl-15-methyl-13-oxabicyclo[10.3.0]pentadecane
14,14-dimethyl-13-oxabicyclo[10.4.0]hexadecane
14,14-diethyl-13-oxabicyclo[10.4.0]hexadecane
14,14-dipropyl-13-oxabicyclo[10.4.0]hexadecane
14,14,16-trimethyl-13-oxabicyclo[10.4.0]hexadecane
14,14-diethyl-16-methyl-13-oxabicyclo[10.4.0]hexadecane
14,16-dimethyl-15-ethyl-13-oxabicyclo[10.4.0]hexadecane
14-ethyl-14-methyl-13-oxabicyclo[10.4.0]hexadecane
14-propyl-14-methyl-13-oxabicyclo[10.4.0]hexadecane
14-propenyl-14-methyl-13-oxabicyclo[10.4.0]hexadecane
14-ethyl-14,16-dimethyl-13-oxabicyclo[10.4.0]hexadecane
14,14-diethyl-16-methyl-13-oxabicyclo[10.4.0]hexadecane
14-propenyl-14,16-dimethyl-13-oxabicyclo[10.4.0]hexadecane
14-(4-methyl-pent-3-enyl)-14-methyl-13-oxabicyclo[10.4.0]hexadecane.

The compounds according to the invention can be obtained by an intramolecular ring-closure reaction of cyclododecanols that have $\beta,\gamma$-unsaturated substituents in the 2-position of the ring.

In the case of those substituted cyclododecanols that have at least one vinyl hydrogen atom in the $\gamma$-position of the above-mentioned substituents, the corresponding 13-oxabicyclopentadecanes are produced, whereas in the case of analogous compounds without a vinyl hydrogen atom in the γ-position, the corresponding 13-oxabicyclohexadecanes are obtained.

A preferred process for the manufacture of the 13-oxabicyclo[10.3.0]pentadecanes according to the invention comprises treating compounds of the formula

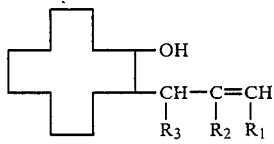

with an acid at temperatures of from 20° to 150° C.

The acid is used in amounts of from 1 to 20 mole %, based on the amount of dodecanol to be reacted.

Examples of acids to be used according to the invention include inorganic acids, such as hydrochloric acid, sulphuric acid and phosphoric acid. Organic acids, such as, for example, p-toluenesulphonic acid, are preferably used, however.

Cyclization is carried out, for the most part, in inert solvents, such as benzene, toluene or xylenes. It can be carried out, however, without a solvent.

A preferred process for manufacturing the 13-oxabicyclo[10.4.0]hexadecanes according to the invention comprises treating compounds of the general formula

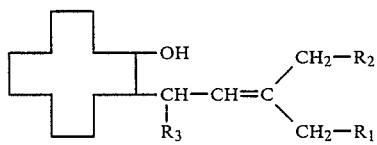

with an acid at temperatures of from 20° to 150° C. For the remainder of the process, the hexadecanes according to the invention are manufactured in a manner analogous to that described above for the manufacture of the pentadecanes according to the invention.

The alkylated cyclododecanols to be used as starting materials are manufactured preferably in a 2-stage process starting from commercially available cyclododecanone.

In the first reaction stage, cyclododecanone is alkylated with an allylic halide in the α-position. If a bicyclopentadecane according to the invention is desired as end product, an allylic halide of the general formula

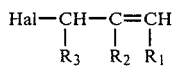

is used. For the synthesis of bicyclohexadecanes according to the invention, an allylic halide of the general formula

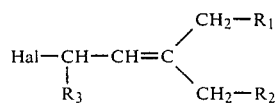

is used.

In the last-mentioned formulae, Hal represents, in each case, chlorine, bromine or iodine, especially chlorine.

Special examples of allylic halides are allyl chloride, methallyl chloride, crotyl chloride, prenyl chloride, geranyl chloride and 3-chloro-1-butene.

The allylic halides to be used according to the invention are, for the most part, commercially available or can be obtained via aldol condensation products or by adding hydrogen halides to conjugated C—C double bonds.

Cyclododecanone is α-alkylated in a customary manner in the presence of strong organic bases having bulky radicals, such as, for example, potassium tert-butoxide, sodium tert-pentoxide and the like. Customarily, the process is carried out by placing an equimolar mixture of cyclododecanone and the allylic halide in an inert solvent, such as toluene and the like, and metering equimolar amounts of organic base into that mixture. The reaction temperatures are generally at from 60° to 110° C.

Surprisingly, alkylation using so-called phase-transfer catalysts results in good yields. In this case, cyclododecanone and the allylic halide are reacted in an organic/alkaline 2-phase system in the presence of a phase-transfer catalyst.

The 2-phase system is formed from an organic water-immiscible inert solvent and an alkali metal hydroxide present either in solid form or as an aqueous solution of from 5 to 50% strength.

Examples of inert solvents are, inter alia, benzene, toluene, xylenes, cyclohexane, petroleum ether, and benzines. Mixtures can also be used.

Examples of alkali metal hydroxides are NaOH, KOH and the like. Based on the alkylating agent used, equimolar amounts of the hydroxide solution are required, an approximately 2-fold excess of the hydroxide solution, however, has an accelerating effect on the reaction. Phase-transfer catalysts may be used that have hitherto already been used for reactions of that type. There may be mentioned as examples crown ethers, quaternary ammonium salts and phosphonium salts, especially tetrabutylammonium bromide. The catalysts are used in amounts of from 0.5 to 5 mole %, based on the allylic halide, with from 2 to 3 mole % having generally proved very efficient.

Advantageously, the 2-phase system, cyclododecanone and the phase-transfer catalyst are placed into the reaction vessel first and the allylic halide is added dropwise to the reaction system. By using this method, 2-fold alkylation can be avoided to a very large extent.

The reaction temperatures are generally between 0° and 150° C., preferably from 20° to 110° C. An optimum ratio of reaction time and yield is often achieved at temperatures between 60° and 80° C.

The reaction mixture can be worked up using conventional techniques: customarily, the phases are separated and the organic phase is fractionally distilled to isolate the desired product.

As the second reaction stage, the cyclododecanone alkylated in the α-position is reduced to form the corresponding cyclododecanol. Reducing agents are used that specifically reduce the carbonyl function without attacking the olefinic double bond in the β,γ-position of the substituent.

Examples of such reducing agents are complex hydrides, such as, inter alia, sodium borohydride and lithium aluminum hydride.

Alternatively, the reduction can be carried out in a manner known per se, according to Meerwein-Ponndorf-Verley, reduction being carried out with isopropanol in the presence of aluminum isopropoxide.

Accordingly, an especially preferred process for the manufacture of compounds of the general formula

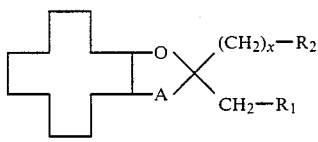

wherein $R_1$ and $R_2$ represent hydrogen or optionally branched alkyl groups having from 1 to 6 carbon atoms or optionally branched alkenyl radicals having from 3 to 6 carbon atoms, A represents a bivalent hydrocarbon radical of the formula

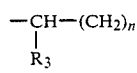

$R_3$ represents hydrogen or methyl, and n and x have, in each case, the same numerical value of 0 or 1, is characterized in that, (a1) with the proviso that x and n are both 0, cyclododecanone is reacted with an allylic halide of the formula

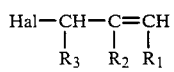

wherein Hal represents chlorine, bromine or iodine, and $R_1$, $R_2$ and $R_3$ have the meanings given above, or (a2) with the proviso that x and n are both 1, cyclododecanone is reacted with an allylic halide of the formula

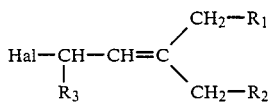

wherein Hal, $R_1$, $R_2$ and $R_3$ have the meanings given above, in an organic/alkaline 2-phase system in the presence of a phase-transfer catalyst, (b) the reaction product according to (a1) or (a2) is reduced with isopropanol in the presence of aluminum isopropoxide to form the corresponding alcohol, and (c) the reaction product according to (b) is subjected to acid treatment at temperatures of from 20° to 150° C.

The compounds according to the invention are used as odorizers. Within the group of compounds according to the invention there is a wide range of different types of scent, from a water vetiver-like sandalwood fragrance to a woody musk fragrance.

All the compounds according to the invention can be used as fixatives. Furthermore, they have excellent adhesive properties.

The compounds according to the invention can therefore be used alone or in mixture, or in admixture with other known odorizers, for example, as components of perfume or for the sensory improvement of a multitude of products, including color dispersions.

In the following, several examples of the present invention will be more fully described, which are given by way of illustration and not of limitation.

EXAMPLE 1

Manufacture of 14-methyl-13-oxabicyclo[10.3.0]pentadecane (a) 40 g (1 mole) of sodium hydroxide platelets, 182 g (1 mole) of cyclododecanone dissolved in 200 ml of toluene, and 10 g of tetrabutylammonium bromide are placed in a 500 ml three-necked flask provided with a stirrer, reflux cooler and dropping funnel. Over a period of one hour, 1 mole of allyl chloride is added dropwise, with stirring, at a reaction-mixture temperature of from 70° to 80° C. The reaction mixture is subsequently stirred for a further 5 hours at 80° C. and finally 200 ml of water are added and the phases are separated. The organic phase is then washed until neutral with a further 100 ml of water and subsequently distilled. After the low-boiling components have been drawn off, unreacted cyclododecanone is first distilled off. Finally, at 0.01 torr and from 82° to 84° C., the desired 2-(2-propenyl)-cyclododecanone is obtained as a colorless liquid in a yield of 149.8 g, corresponding to 67.5% of the theoretical yield.

(b) 0.1 mole of aluminum isopropoxide in 500 ml of isopropanol is placed in a three-necked flask provided with a stirrer and a Vigreux column. The mixture is refluxed. A 25% by weight solution of 2-(2-propenyl)-cyclododecanone in isopropanol is added dropwise to the boiling reaction mixture, over a period of 12 hours. The acetone produced, which serves at the same time as indicator for the progress of the reaction, is collected at the top of the column. After approximately a further hour of refluxing, the reaction is complete. After the isopropanol has been drawn off, the reaction mixture is hydrolyzed with 6N hydrochloric acid. Extraction is then carried out with 200 ml of toluene and the organic phase is worked up by distillation. Finally, 2-(2-propenyl)-cyclododecanol is obtained as a colorless liquid in a yield of 95% of the theoretical yield at a boiling range of from 172° to 175° C. at 12 torr.

(c) 1 mole of 2-(2-propenyl)-cyclododecanol is dissolved, together with 20 g of p-toluenesulphonic acid, in 1000 ml of toluene, and the mixture is refluxed for 15 hours. The mixture is then neutralized with 10% sodium carbonate solution, the phases are separated and the organic phase is worked up by distillation. After the toluene has been drawn off, 14-methyl-13-oxabicyclo[10.3.0]pentadecane is obtained, in a yield of 98% of the theoretical yield, at a boiling range of from 85° to 88° C. at 0.05 torr. Colorless oil; scent: warm, vetiver-like sandalwood fragrance.

EXAMPLE 2

The working method according to Example 1 is repeated, except that reduction is carried out using sodium borohydride instead of isopropanol/aluminum isopropoxide (according to b).

1 mole of 2-(2-propenyl)-cyclododecanone is added dropwise, over a period of one hour, with stirring, at room temperature to a solution of 15.2 g (0.4 mole) of sodium borohydride dissolved in 1200 ml of isopropanol. The mixture is then refluxed with stirring for 2 hours. After the excess isopropanol has been drawn off, 2N hydrochloric acid is added to the reaction mixture until the evolution of hydrogen is complete. The mixture is then extracted with ether, the organic phase is dried with sodium sulphate and, after the ether has been drawn off, is distilled.

The desired 2-(2-propenyl)-cyclododecanol is obtained as a colorless, highly viscous liquid which slowly hardens to a wax-like substance at room temperature, in a yield of 95% of the theoretical yield.

EXAMPLES 3 TO 6

Analogously to the working method according to Example 1, the following compounds according to the invention are obtained:

14-dimethyl-13-oxabicyclo[10.3.0]pentadecane
  Colorless oil; boiling point 165° to 168° C./12 torr;
  scent: mild sandalwood fragrance with vetiver tone.

14-ethyl-13-oxabicyclo[10.3.0]pentadecane
  Colorless oil; boiling point 88° to 90° C./0.05 torr;
  scent: warm sandalwood/amber fragrance.

14,15-dimethyl-13-oxabicyclo[10.3.0]pentadecane
  Colorless oil; boiling point 166° to 167° C./12 torr;
  scent: strong smokey/woody musk fragrance.

14-dimethyl-13-oxabicyclo[10.4.0]hexadecane
  Colorless mass hardening to a wax-like substance; boiling point 88° to 91° C./0.03 torr;
  scent: animal/woody fragrance.

While only several examples of the invention have been described, it will be obvious that many changes and modifications may be made thereunto, without departing from the spirit and scope of the invention.

What is claimed is:

1. A compound of the formula

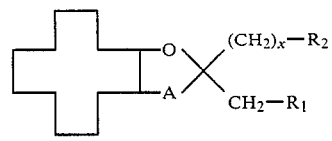

wherein
  $R_1$ and $R_2$ represent hydrogen or optionally branched alkyl groups having from 1 to 6 carbon atoms or optionally branched alkenyl groups having from 3 to 6 carbon atoms,
  A represents a bivalent hydrocarbon radical of the formula

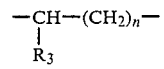

wherein
  $R_3$ represents hydrogen or methyl, and
  n and x are both 1.

2. The compound of claim 1, wherein $R_1$ and $R_2$ represent hydrogen or methyl.

* * * * *